United States Patent [19]

Schwartz et al.

[11] Patent Number: 4,675,438

[45] Date of Patent: * Jun. 23, 1987

[54] DIRECT CONTINUOUS FLOW INTEGRATION OF PRODUCTION AND PURIFICATION OF HIGH PURITY ISO- OR TEREPHTHALIC ACID

[75] Inventors: Michael M. Schwartz, Aurora; Leonard E. Stark, Bristol, both of Ill.

[73] Assignee: Amoco Corporation, Chicago, Ill.

[*] Notice: The portion of the term of this patent subsequent to Mar. 28, 1995 has been disclaimed.

[21] Appl. No.: 368,975

[22] Filed: Apr. 16, 1982

Related U.S. Application Data

[63] Continuation of Ser. No. 961,765, Nov. 17, 1978, abandoned.

[51] Int. Cl.$^4$ .............................................. C07C 51/16
[52] U.S. Cl. ................................................... 562/416
[58] Field of Search ......................................... 562/416

[56] References Cited

U.S. PATENT DOCUMENTS 3,845,100 10/1974 Kusak .................................. 562/417
4,081,464 3/1978 Marsh .................................. 562/417

FOREIGN PATENT DOCUMENTS 1056319 1/1967 United Kingdom ................ 562/417

*Primary Examiner*—Alan Siegel
*Attorney, Agent, or Firm*—James R. Henes; William H. Magidson

[57] ABSTRACT

This invention pertains to the production of high purity iso- or terephthalic acid by the catalytic liquid phase oxidation of m- or p-xylene with molecular oxygen gas in the presence of a solvent system consisting essentially of 85 to 97 weight percent liquid benzoic acid and 15 to 3 weight percent water to provide a fluid feed for the purification of such phthalic acid by hydrogenation of the fluid effluent of such oxidation in the presence of a heterogeneous catalyst containing a Group VIII noble metal at an elevated temperature at which all the aromatic oxygen-containing products are in solution under the requisite elevated pressure to maintain a liquid phase of said solution followed by the precipitation of such phthalic acid from solution and the separation washing and drying of the precipitate. Such integration of process steps eliminates expensive and time consuming intermediate steps of precipitating impure iso- or terephthalic acid from oxidation effluent, separation, washing and drying said impure precipitate as well as purification of solvent for recycle to oxidation.

7 Claims, No Drawings

DIRECT CONTINUOUS FLOW INTEGRATION OF PRODUCTION AND PURIFICATION OF HIGH PURITY ISO- OR TEREPHTHALIC ACID

This is a continuation of application Ser. No. 961,765, filed Nov. 17, 1978, now abandoned.

BACKGROUND OF THE INVENTION

British Patent Specification No. 1,088,183 discloses a process for the continuous preparation of iso- or terephthalic acid by the oxidation of m- or p-xylene with a source of molecular oxygen in the presence of a benzoic acid solution of one or more transition metal oxidation catalysts and a source of bromine conducted at a temperature in the range of from 170° C. up to 275° C. and at a gauge pressure in the range of from 21 up to 35 kg/cm$^2$ with the removal of by-product water as it is formed.

According to U.S. Pat. No. 4,081,464 there were two disadvantages associated with the process of said British Patent and both disadvantages were associated with the assigned operating gauge pressure of from 21 up to 35 kg/cm$^2$. The first disadvantage, occurring at the start-up of the oxidation, was associated with a sudden somewhat drastic increase in oxidation temperature, a substantially instantaneous increase of about 110° C., which caused over-oxidation of the magnitude of charring of product and solvent as water content of the benzoic acid solvent decreased from 5 weight percent to 0 weight percent as would occur when trying to remove by-product water as rapidly as it was formed. Such drastic temperature increase occurred without an accompanying increase in the pressure in the oxidation zone.

The second disadvantage was associated with continuity of operation after a successful start-up had been accomplished. The manifestation of the second disadvantage was a rather wise cycling of temperature above and below a set selected operating temperature.

Both of said disadvantages were overcome according to U.S. Pat. No. 4,081,464 by conducting the continuous oxidation of m- or p-xylene not in the presence of liquid benzoic acid as the solvent but rather in the presence of a solvent system consisting essentially of from 85 up to 97 weight percent benzoic acid and from 15 down to 3 weight percent water, at a temperature of from 175° C. up to 235° C., at a gauge pressure in the range of from 6 up to 25 kg/cm$^2$ and by varying the rate of water condensate recycled to the oxidation zone in response to its temperature change from a selected preset temperature so that the rate of water recycled increased or decreased with an increase or decrease from said temperature. By following those operating guides continuous oxidation could be successfully started without an initial drastic temperature increase and smoothly continued with not more than a ±5° C. temperature variation from a selected constant operating temperature to consistently achieve the 85 to 95 mole percent yield of iso- or terephthalic acid product of the purity promised by the above British Patent.

However, the iso- or terephthalic acid product recovered from the process of either the above British Patent or U.S. Patent did not have the current exceptionally high purity equivalent to "fiber grade quality" which is indicated by a carboxybenzaldehyde content of not more than 0.015 weight percent (150 ppm). Thus a suitable process was needed for converting to said fiber grade quality the iso- or terephthalic acid products recovered from such processes. The known art pertinent to such purification was surveyed for likely purification techniques to integrate with the oxidation processes of said patent.

There have been proposed many techniques for purifying rather insoluble impure iso- and terephthalic acids. Most all of the proposed techniques start with said acids as solids recovered from an oxidation process. Since about 1959 the proposed purification techniques have started with impure iso- or terephthalic acid product recovered from an oxidation conducted in the presence of acetic acid as reaction solvent. Part of the previously proposed purifications involved esterifying the impure iso- or terephthalic acid with methanol recovering the impure diester product and subjecting the diester to fractional crystallization or distillation. Another portion of the purification techniques involved dissolving the recovered impure iso- or terephthalic acid as a water soluble salt in water, and subjecting the solution to oxidizing and/or reducing agents and then precipitating the free acids by acidifying the solutions so treated.

Still another portion of the pertinent purification techniques involve the catalytic hydrogenation of solutions of the impure iso- or terephthalic acid. Three of such catalytic hydrogenations of most interest were described in U.S. Pat. Nos. 3,546,285 and 3,584,039 and in British Patent Specification No. 1,056,319. The purification techniques of the two U.S. Patents started with solid impure iso- or terephthalic acid whose main impurity was, respectively, 3-carboxybenzaldehyde (3-CBA) or 4-carboxybenzaldehyde (4-CBA) recovered from the catalytic air oxidation of m- or p-xylene in acetic acid reaction medium or solvent or recovered from the nitric acid oxidation of m- or p-xylene. Such recovered impure iso- or terephthalic acid was dissolved either in an aliphatic saturated fatty acid (e.g. acetic acid) containing 0 to 30 percent by volume of water (No. 3,546,285) or in water (No. 3,854,039) and then the solution was subjected to hydrogenation at elevated temperature (generally above 250° C.) under liquid phase conditions and preferably in the presence of supported or unsupported Group VIII noble metal as catalyst. Both references indicate a preference for metallic palladium disposed on the surface of a charcoal as the hydrogenation catalyst. Purified iso- or terephthalic acid product is precipitated by cooling the solution after the solution is separated from catalyst (Pat. No. 3,854,093) or before the solution is separated from the catalyst (Pat. No. 3,546,285). The latter patent also suggests using benzoic acid with 0 to 30 volume percent water in place of the fatty acid with 0 to 30 volume percent water to form the solution for catalytic hydrogenation. Further the same patent demonstrates that cobalt oxidation catalyst retained by the impure phthalic acid has little or no useful hydrogenation catalytic effect with respect to impurity removal.

However, both of the foregoing catalytic hydrogenation purification processes appear to imply that it is desirable to effect some partial purification of iso- or terephthalic acid by its separation from the reaction solvent mother liquor (e.g., acetic acid mother liquor) which causes some of the impurities and most of the oxidation catalyst components to be retained in solution in the mother liquor. But such pre- or partial purification not only adds to the processing time but requires substantial capital expenditure for one or more high pressure and at least one moderate pressure crystallizer, a filter, or centrifuge for accomplishing the solid-liquid separation, drying of recovered reslurrying of the recovered solids, and plant space.

The purification techniques of British Patent Specification No. 1,056,319 is applied directly to the fluid effluent from the oxidation of m- or p-xylene with a source of molecular oxygen containing from 20 percent (air) up to 100 percent (oxygen gas) oxygen in the presence of acetic acid (1 to 10 weight parts acetic acid per weight part of xylene), in the presence of 0.1 to 1.0 weight percent transition metal oxidation catalyst (e.g., Co, Mn or Co and Mn) and 0.1 to 1.0 weight percent bromine based on the xylene at a temperature in the range of from 150° C. up to 230° C. Such fluid effluent, an acetic acid mother liquor, a suspension of iso- or terephthalic acid precipitated during oxidation of the xylene, is heated to a temperature in the range of from 260° C. up to 315° C. under pressure to maintain acetic acid in the liquid phase and in the presence of sufficient acetic acid to dissolve all solids present in said effluent. The weight ratio of acetic acid to xylene of 8 to 10:1.0 used in the oxidation provides said "sufficient acetic acid" but the acetic acid to xylene ratio of 1 to 7:1.0 used in the oxidation requires the addition of acetic acid to the oxidation effluent before heating it to the 260° to 315° C. temperature. Acetic acid mother liquor or its acetic anhydride fortified product having about 5 to 10 weight percent water content is disclosed as preferred for dissolving the solids at the 260° to 315° C. temperature.

The resulting 260° to 315° C. temperature solution is then with or without prior treatment with hydrogen at 15 to 200 pounds per square inch hydrogen partial pressure cooled to a temperature in the range of from 150° C. to 176° C. to precipitate crystalline iso- or terephthalic acid for recovery. The recovered crystalline product is washed with acetic acid and dried.

Such direct redissolving and recrystallization is demonstrated to cause an 85% decrease in 4-CBA in the absence of hydrogen treatment and a 91% decrease in 4-CBA with hydrogen treatment of the solution prior to recrystallization.

The concept of the process of British Pat. No. 1,056,319 might be integratable with the oxidation processes of the foregoing British Pat. No. 1,088,183 or U.S. Pat. No. 4,081,464 and eliminate the extra capital costs and process time noted before providing the recrystallization or hydrogenation and recrystallization from the liquid benzoic acid solvent of the British Patent or the benzoic acid-water solvent of the U.S. Patent could be perceived as providing a product of purity equivalent to fiber grade quality. To perceive success for such direct purification routes would further require knowledge of the relative solvent properties, of liquid benzoic acid or the benzoic acid-water solvent system vis-a-vis the solvent properties of acetic acid containing 5 to 10 weight percent water for the catalyst components and impurities produced during the oxidation and their reduction products.

It was determined in our laboratories that the solvent properties of liquid benzoic acid and the 85–97% benzoic acid—15 to 3% water solvent system for dissolving iso- or terephthalic acid to be too limited at commercially feasible processing temperatures and pressures. It was also determined that a solvent system containing from 25 up to 75 weight percent water and 75 to 25 weight percent benzoic acid could dissolve suitable, from process economic and design basis, amounts of iso- and terephthalic acids at commercially feasible temperatures. The solvent system containing 25 to 75% benzoic acid and the balance water would, at said feasible temperature, require to maintain liquid phase conditions operating pressures slightly below the pressure required when water was the only solvent component because the mole fraction of benzoic acid is quite small (less than 0.01) in the mixture of water and benzoic acid vapors in equilibrium above such liquid solvent.

The saturation temperatures for 10, 20, 30, 40 and 50 grams of terephthalic acid per 100 grams of 25% water-75% benzoic acid, 50% water-50% benzoic acid and 75% water-25% benzoic acid are shown in TABLE I wherein benzoic acid is shown as "BA."

TABLE I

| | SATURATION TEMPERATURES, °C. | | |
|---|---|---|---|
| Terephthalic | Water-Benzoic Acid Solvent Systems | | |
| Acid, grams/100 grams solvent | 25% $H_2O$—75% BA | 50% $H_2O$—50% BA | 75% $H_2O$—25% BA |
| 10 | 246 | 231 | 232 |
| 20 | 274 | 257 | 255 |
| 30 | 293 | 273 | 268 |
| 40 | 303 | 282 | 278 |
| 50 | 313 | 292 | 285 |

The saturation temperatures for 10 to 50 grams of isophthalic acid per 100 grams of the water-benzoic acid solvent systems consisting of 25, 50 and 75 weight percent water will be found to be about 100° C. lower than the saturation temperatures for the same concentrations of terephthalic acid in the same solvent systems.

SUMMARY OF THE INVENTION

Using the foregoing information we have devised a technique for the direct purification of iso- or terephthalic acid products produced in the presence of liquid benzoic acid solvent or liquid benzoic acid-water solvent system containing 85 to 95 weight percent benzoic acid and 15 to 5 weight percent water which are, respectively by the oxidation processes of British Patent Specification No. 1,088,183 and U.S. Pat. No. 4,081,464 whose disclosures pertinent to the oxidation of m- or p-xylene in liquid benzoic acid or liquid water-benzoic acid solvent system are incorporated in and made a part hereof by reference thereto.

Said direct purification comprises diluting the fluid oxidation effluent from said oxidations with water in an amount to provide a solvent system of from 25 up to 75 weight percent water and from 75 down to 25 weight percent benzoic acid which is a weight ratio of water to benzoic acid of from 0.33:1.0 up to 3:1, heating said diluted fluid effluent to a temperature at which all the solids in said effluent dissolve in said solvent system, hydrogenating said solution under liquid phase conditions in the presence of a Group VIII noble metal in particulate form, separating the hydrogenated solution from said catalyst, precipitating iso- or terephthalic acid from the separated solution by cooling and concentrating it through the evaporation of water vapor from the solvent system, separating the precipitate from the remaining liquid solvent system, washing the separated precipitate with water, and drying the washed precipitate.

The hydrogenation can be conducted in batchwise or continuous operations in a stirred-tank type reaction vessel or in a column having a zone for combining the solution and hydrogen gas, a catalyst zone, and a zone for disengaging gas from liquid. The stirred-tank type reactor readily lends itself to both batchwise and continuous operation while the column type reactor is most suited for continuous operation using trickle bed or flooded bed concurrent or countercurrent flow of solution and hydrogen through a bed of the particulate catalyst, preferably 0.1 to 1.0 weight percent palladium metal dispersed on the surface of an insoluble carrier such as a charcoal having a high surface area to mass ratio. Concurrent flow of solution and hydrogen downward through the catalyst bed is the preferred mode for continuous operation and such flow with the bed in a completely flooded condition is also preferred.

For use of the stirred-tank hydrogenation vessel in batchwise operation the solution containing suspended particulate catalyst (e.g. suitably said Pd dispersed on the surface of charcoal) and hydrogen gas are separately charged to said vessel at hydrogenation temperature, stirred and maintained at such temperature for 0.5 to 2.0 hours. Also the solution and hydrogen gas can be separately charged to the stirred-tank vessel containing a porous vessel (e.g., basket) of coarse particulate catalyst (e.g. said Pd on charcoal). Either batchwise technique can be readily connected to a continuous mode of operation.

The above inventive direct purification process suitably is conducted with a water diluted fluid oxidation effluent containing from 10 up to 50 weight parts of iso- or terephthalic acid for each 100 weight parts of solvent system consisting of from 25 up to 75 weight percent water and from 75 down to 25 weight percent benzoic acid. The temperature and associated iso- and terephthalic acid saturation concentration data before presented for such solvent systems, the contents of the fluid oxidation effluent determined by analysis and the selected temperature of operating the catalytic hydrogenation will enable one to determine the amount of diluent water to be used with the fluid oxidation effluent.

The amount of hydrogen to be used in the present inventive process is relatively small. Ideally, the amount of hydrogen to be used can be calculated on the basis of the theoretical amount needed to convert the carboxybenzaldehyde impurity to the corresponding toluic acid; that is, two moles of hydrogen per mole of the carboxybenzaldehyde impurity present. A suitable excess of hydrogen that does not cause unwanted reduction of the desired iso- or terephthalic acid product, can be provided by the use of hydrogen partial pressure of from 3.5 up to 14 kg/cm$^2$ especially with the particulate hydrogenation catalyst comprising from 0.2 up to 0.8 weight percent metallic palladium dispersed on the surface of a high surface area to mass ratio charcoal; e.g., upward from 1000 m$^2$ per gram.

Further with respect to the particulate catalyst used in the present inventive direct purification process, those having a support for the Group VIII noble metal should have as the support, one that does not have non-metallic components, occluded or otherwise which can be leached or extracted by the high temperature solution of iso- or terephthalic acid in the 75 to 25 percent benzoic acid-25 to 75 percent water solvent system. U.S. Pat. No. 3,584,039 defines and describes not only suitable insoluble, particulate supported and unsupported Group VIII noble metal containing hydrogenation catalysts but also discloses that silica, silicon carbide and alpha-alumina which would be thought of as insoluble catalyst supporting materials are unsuitable with said high temperature solution of terephthalic acid because such solutions will dissolve substantial amounts of said supports. Carbon or very low metal content charcoal are the only practical catalyst support material for such use with the high temperature solutions.

Suitably, the oxidation's fluid effluent, a suspension of iso- or terephthalic acid in the liquid 85 to 95 percent benzoic acid and 15 to 5 percent water solvent system or the liquid benzoic acid, before the catalytic hydrogenation is diluted with sufficient water to provide an amount of the 25 to 75 percent water-75 to 25 percent benzoic acid solvent system such that there are present for each 100 weight parts thereof for each 8 to 50, preferably 20 to 40, weight parts of iso- or terephthalic acid. Such diluted fluid effluent is then suitably heated to 2° to 10° C., preferably 5° C., above the temperature of saturating the 100 weight parts of solvent system with the 8 to 50, preferably 20 to 40, weight parts of iso- or terephthalic acid.

For efficient material handling and processing of product being purified, it is preferred to use an amount of water for dilution of fluid oxidation effluent which will provide 100 weight parts of the solvent system comprising 25 to 75% water-75 to 25% benzoic acid for each 20 to 40, most preferably for each 25 to 30, weight parts of iso- or terephthalic acid.

The water used to dilute the fluid oxidation effuent can in a small part be supplied as condensate of by-product produced by the oxidation of m- or p-xylene. Such condensate of by-product water amounts, as a practical matter, to about 0.2 weight parts for each 1.0 weight part of iso- or terephthalic acid produced. Moreover, such by-product water condensate is rather pure and, when used as diluent according to the present invention, does not contribute impurities to the composite of diluent and fluid oxidation effluent.

Further the heat produced by the oxidation of a xylene to a phthalic acid is sufficient to evaporate 3 18 weight parts of water per 1.0 weight part of phthalic acid produced (assuming 100% efficiency in such use of the heat of reaction to evaporate water). Such evaporation of 3.18 weight parts of water per 1.0 weight part of iso- or terephthalic acid produced can be accomplished by indirect heat exchange with the fluid oxidation reaction mixture within (e.g. internal coils) or without (e.g., by a thermal siphon having a heat exchanger as an integral part thereof) or by injecting water on the surface of the stirred fluid in the oxidation zone. Said 3.18 weight part of evaporatable water per 1.0 weight part of phthalic acid comprises 0.2 weight parts of by-product water and 0.06 weight part water from the oxidation solvent system comprising 3 to 15 weight percent water and 97 to 85 weight percent benzoic acid. Since by-product and solvent component sources of water amount to 0.26 weight part water per 1.0 weight part of iso- or terephthalic acid, the difference (3.18–0.26) of 2.98 weight parts of water per 1.0 weight part of iso- or terephthalic acid product produced is that additionally used and evaporated to complete the removal of heat of reaction. Such additionally used water should be of such purity that it does not add extraneous materials which have a known deleterious effect on the hydrogenation catalyst or the end use of the iso- or terephthalic acid.

The weight ratio of water to iso- or terephthalic acid varies widely in the solution thereof to be purified in the presence of the solvent system consisting of from 25 to 75% water and from 75 to 25% benzoic acid used in an amount of from 100 weight parts for each 8 to 50 weight parts of iso- or terephthalic acid. For example, in such purification of terephthalic acid in amounts of from 8 to 50 parts by weight per 100 weight parts of 25 to 75% water-75 to 25% benzoic acid solvent system the ratio of water to terephthalic acid is in the range of from 0.425 up to 12.8 weight parts of water per 1.0 weight part of said phthalic acid. Thus it can be seen that the additionally evaporated (2.98 parts per part of phthalic acid) is not all needed at the lower ratio of 0.425 to 1.0 and is inadequate for the upper end of the ratio of 12.8:1.0.

The fluid oxidation effluent from the air oxidation of m- or p-xylene in the presence of a source of bromine and a source of cobalt, manganese or cobalt and manganese in (a) liquid benzoic acid is produced at a temperature in the range of from 170° C. up to 274° C. and an operating gauge pressure of from 21 up to 35 kg/cm$^2$ or (b) in liquid solvent system comprising from 97 to 85 weight percent benzoic acid and 3 to 15 weight percent water at a temperature of from 175° C. up to 235° C. and a constant gauge pressure from the range of from 7 to 21 kg/cm$^2$. For the conduct of such oxidation within the contemplation of this invention the reaction solvent in process (a) or (b) can suitably be used in the weight ratio of 2 to 6 weight parts of solvent per 1.0 weight part of m- or p-xylene. Preferably the weight ratio of solvent to such xylene is in the range of from 2.5:1.0 to 4.5:1.0 because the resulting fluid effluents can be readily diluted with water to the solvent systems consisting of from 50 up to 75% water and 50 down to 25% benzoic acid which, as the solubility data in TABLE I indicates, will dissolve for each 100 weight parts of such solvent from 30 to 50 weight part of terephthalic acid and are useful at temperatures not exceeding 300° C. Such solutions at 28 to 58 kg/cm$^2$ gauge pressure to maintain the solvent in the liquid phase result in a hydrogenation operating gauge pressure, after adding an amount of hydrogen corresponding to a hydrogen partial pressure of from 3.5 up to 7.0 kg/cm$^2$, of from 31.5 to 65 kg/cm$^2$. Also for the purification of terephthalic acid said solutions containing 30 to 50 weight parts of terephthalic acid per 100 weight parts of the 50:50 to 75:25 water-benzoic acid solvent system can, after separation from the catalyst, need be cooled to only about 120° C. without removal of solvent components to precipitate 98 to 99% of the originally dissolved terephthalic acid. However, such catalyst free solutions of terephthalic acid can be flash evaporated in 2 or more, preferably 3 to 4, steps down to a final temperature of 150° C. with removal of vapors, essentially pure water, from each step and more than 99% of the terephthalic acid originally dissolved with precipitate.

The water removed and condensed from the re-precipitation of the purified product can be reused to prepare the oxidation solvent (85-97% benzoic acid—1-5-3% water), to remove heat from the oxidation reaction and to dilute the fluid effluent from the oxidation in the preparation of the solution for the catalytic hydrogenation.

The mother liquor separated from the precipitated purified iso- or terephthalic acid can in part be processed (e.g. by distillation) to remove as a first fraction the water not evaporated during such product precipitation and then recover benzoic acid free from materials boiling higher than benzoic acid (original impurities and/or their reduction products) and catalyst components which are in the distillation bottoms. The part of the recovered mother liquor not so processed is recycled to make the solvent feed for the oxidation step.

The following examples illustrate the best modes currently contemplated for the conduct of the present invention and are not intended as determinative of the scope of the present invention.

EXAMPLE 1

A. Oxidation of p-Xylene

The continuous oxidation of p-xylene is conducted in a stirred-tank type reaction vessel having means for heating its contents, valved inlets for charging liquids and air, a valved outlet for discharge of fluid oxidation effluent from the bottom portion of the reaction vessel, an exhaust outlet in the top portion of the reaction vessel for discharge of oxygen depleted air containing water and benzoic acid vapors, vaporized from the stirred liquid in the reaction zone of the reaction vessel, an exhaust transfer line attached to said exhaust outlet at one end and attached at the other end to the inlet of a condenser whose operating temperature can be varied directly with respect to a change in the temperature of the contents of the stirred reaction zone, a vessel to disengage condensate and gas used to collect condensate attached to the discharge side of the condenser, a reflux inlet to the oxidation zone attached to said condensate receiver, and an outlet for disengaged gas having a pressure control valve through which the disengaged gas discharges from the oxidation system of apparatus. Temperature probes are provided for measuring the oxidation zone's temperature.

The continuous oxidation of p-xylene was initiated by charging to the stirred zone of the oxidation vessel set to operate at a gauge pressure of 18.65 kg/cm$^2$ a solution prepared from 810 grams of liquid benzoic acid (122° C.) and 90 grams of water containing 3.07 milligram moles of cobaltous acetate tetrahydrate, 22.17 milligram moles of manganous acetate tetrahydrate and 30.32 milligram moles of sodium bromide. The resulting stirred fluid is heated to a temperature of 190° C., 27 grams of aromatic hydrocarbon comprising 95 weight percent p-xylene and 5 weight percent toluene are pumped into the stirred fluid. Thereafter air is injected into the stirred fluid. The reaction temperature is set to operate at 205° C. and the condenser's cooling system is set to respond to that fixed 205° C. operating temperature in the stirred oxidation zone. When the stirred oxidation zone reached 205° C., said aromatic hydrocarbon mixture was pumped into the oxidation zone at a rate of 4.5 grams per minute. The air injection was adjusted to provide the exhaust with 5 volume percent oxygen. After 60 minutes of operation said solution of catalyst components (Co, Mn and Br) in the 90% benzoic acid-10% water solvent was pumped into the oxidation zone at the rate of 15 grams per minute as the addition of p-xylene and air injection were continued. Then fluid reaction effluent was withdrawn at the rate of 26.65 grams per minute into a stirred surge tank maintained at a temperature of 205° C. and a gauge pressure of 18.65 kg/cm$^2$.

Said fluid effluent, by analysis, is found to contain on a weight basis 62.1% benzoic acid, 29.4% terephthalic acid, 6.9% water, 0.16% p-toluic acid, 0.119% 4-carboxybenzaldehyde, and 1.08 other oxygen-containing aromatic impurities.

B. Purification

The catalytic hydrogenation step is conducted in a heat jacketed autoclave having a porous chamber capable of retaining 8 mesh (U.S. sieve size) particles and capable of being raised and lowered. Said chamber is charged with 5.5 grams of 8 mesh particulate catalyst having 0.5 wt. % Pd dispersed on a carbon support.

Fluid oxidation effluent in an amount of 800 grams is withdrawn from said stirred surge tank by a pump which discharges the fluid into the heat jacketed autoclave having a magnetic stirrer capable of being driven by a variable speed external rotating magnetic field. Distilled water which had been deionized is also added to the autoclave in the amount of 670 grams for the 800 grams of said fluid effluent. The diluted fluid effluent is heated to a temperature of 282° C. and a gauge pressure of 61.9 kg/cm$^2$. The 1470 grams of diluted fluid effluent is stirred and maintained in the autoclave at 282° C. and 61.9 kg/cm$^2$ gauge pressure for 160 minutes to insure complete dissolving of the solids from the fluid oxidation effluent. Thereafter hydrogen gas is charged into the solution until the gauge pressure in the autoclave reaches 68.9 kg/cm$^2$. This provides a hydrogen partial pressure of 7 kg/cm$^2$. The combination of solution and hydrogen is stirred for 25 minutes so that an equilibrium dissolved hydrogen concentration is reached. Then the porous catalyst chamber is lowered into the stirred liquid and left therein for 100 minutes at which time, by analysis of a sample of the resulting fluid, it is found that the fluid has a 4-carboxybenzaldehyde content of 0.0148 weight percent.

The hydrogenated solution is stirred and cooled to a temperature of 25° C. The resulting slurry of purified terephthalic acid is discharged and collected in a filter. The autoclave is washed with hot deionized distilled water. The wash water is added to the filter to also wash the filter cake. The washed terephthalic acid filter cake is dried and by analysis is found to contain 0.0031 weight percent 4-carboxybenzaldehyde and 0.0055 weight percent p-toluic acid.

EXAMPLE 2

A second 800 gram sample of fluid oxidation effluent obtained as described in Example 1 and diluted with 670 grams of distilled water which had been deionized as described in Example 1. The diluted fluid oxidation effluent is treated in the manner described in the B portion of Example 1. After 100 minutes of contact of the dilute fluid effluent and hydrogen with the particulate 0.5% Pd on carbon support a sample of the solution is found by analysis to contain only 0.0125 weight percent 4-carboxybenzaldehyde. The washed and dried terephthalic acid filter cake is found by analysis to contain 0.0019 weight percent 4-carboxybenzaldehyde and 0.0085 weight percent p-toluic acid.

For purposes of reference, the terephthalic acid product separated from the fluid oxidation effluent not subjected to the catalytic hydrogenation step of the present invention but rather washed once with liquid benzoic acid at 145° C. (weight ratio benzoic acid to separated terephthalic acid of 0.8 to 1.0), then washed with p-xylene at 100° C. (weight ratio of xylene to separated terephthalic acid of 0.6:1.0) and dried had a 4-CBA content of 0.15 weight percent, and a p-toluic acid content of 0.03 weight percent, an optical density value of 0.61 as determined with 340 nm light, and a b-value of $\leq 1$ as determined by incandescent light.

The products of Example 1 and 2 above had, respectively, the optical density (340 nm) values of 0.612 and 0.712 and the b-values of 0.55 and 0.15.p Optical density values are determined by the use of a spectrophotometer and relate to the use of an ammoniacal solution of diammonium terephthalate (prepared from sample tested) in a 4 cm. cell through which 340 nm light is passed after calibrating the spectrophotometer with the same light but with the ammonia solvent in the 4 cm. cell. The optical density values are a qualitative indication of residual presence of impurities.

The b-values are a measure of color of solid terephthalic acid exposed to incandescent light on a scale whereby negative values are a measure of blueness (a value of $-4$ is a greater blue intensity than a value of $-2$) and positive values are a measure of yellowness (a value of $+4$ is a greater yellow intensity than a value of $+2$).

For the step of direct esterification of purified terephthalic acid with ethylene glycol in the manufacture of fiber forming polyethylene terephthalate, a commercially acceptable purified terephthalic acid product should have a 4-carboxybenzaldehyde content not exceeding 0.0025 weight percent, a p-toluic acid content not exceeding 0.0150 weight percent, an optical density value not exceeding 1.0 as determined with 340 nm light, and a b-value color in the range of from $-2$ up to $+2$.

The following example is another mode of conducting the present inventive concept illustrated by the combination of continuous p-xylene oxidation with air in the presence of the solvent system consisting of 90% benzoic acid and 10% water, dilution of the fluid oxidation effluent with water, heating the diluted fluid effluent to dissolve all the solids present, and subjecting the solution to catalytic hydrogenation as the solution moves through a bed of particulate Pd on carbon hydrogenation catalyst.

EXAMPLE 3

A. Continuous Oxidation

Oxidation apparatus similar to that described in part A of Example 1 is again used. The stirred-tank reactor is operated at a gauge pressure of 25 kg/cm$^2$ by setting the pressure regulating valve to maintain a gauge pressure of 25 kg/cm$^2$. The reflux condenser is set to operate at a gas exit temperature of 97° C. The total condenser is set to operate with hot water feed which exits at a temperature of 46.5° C. The oxidation zone temperature is set at 226° C. but the stirred liquid therein varies between 223° C. and 228° C. during operation.

Two liquid feeds are prepared: (i) a solution maintained at a temperature of 145° C. and containing 3.69 kg liquid benzoic acid for each 1.05 kg p-xylene and (ii) an aqueous solution containing 5.3 grams of cobaltous acetate tetrahydrate, 16.9 grams of manganous acetate tetrahydrate and 9.7 grams of sodium bromide dissolved in 503.4 grams of water. The solution of benzoic acid in p-xylene is pumped into the oxidation vessel at the rate of 4.74 kg/hr., and the aqueous solution is pumped into the oxidation vessel at the rate of 545.3 grams per hour. Compressed air is supplied to the stirred fluid in the oxidation vessel to provide a spent air (oxidation zone exhaust free of benzoic acid and water) containing 5.5 volume percent oxygen. Such rates of feeding said solutions provide a 88% benzoic acid-12% water solvent in the weight ratio thereof to p-xylene of 4:1.

The fluid effluent is withdrawn from the stirred oxidation zone at the rate of 5.99 kg/hr. Said fluid effluent contains on a weight basis 61.65% benzoic acid, 8.4% water, 25.72% terephthalic acid, 0.072% 4-carboxybenzaldehyde, 0.041% p-toluic acid, 1.3% trimellitic acid, 1.7% high boiling oxygen-containing aromatic compounds, and 1.11% other impurities including catalyst components. Such fluid effluent contains about 29 weight percent undissolved solids associated with a solution of which solvent is 88% benzoic acid and 12% water by weight. Said fluid effluent is collected in a stirred surge tank having a reflux condensor through which substantially water vapor free gas is withdrawn to "degas" (i.e., remove spent air).

A sample of said fluid effluent is cooled to 125° C. at a lower pressure so that water is flash evaporated for removal as vapor. The suspension of terephthalic acid in liquid benzoic acid is filtered. The filter cake is washed with liquid benzoic acid at 145° C. and then with p-xylene at 60° C. The dried filter cake upon analysis is found to have 0.053 wt. % 4-carboxybenzaldehyde content, an optical density value (340 nm light) of 1.43 and a b-value of 0.9.

B. Purification

To dissolve the 1.737 kg solids they are combined with the 5.99 kg/hr. fluid oxidation effluent, 3.24 kg/hr. of water at 230° C. to provide 7.5 kg of solvent which contains on a weight basis 50% each of benzoic acid and water. The resulting diluted fluid effluent contains 123 weight parts solids per 100 weight parts of solvent and is heated to a temperature of 268° C. under a gauge pressure of 47 kg/cm$^2$ to maintain water in the liquid phase and to dissolve all of the 1.737 kg/hr. solids content of the fluid effluent. The resulting 9.23 kg/hr. of solution at 275° C. and 53 kg/cm$^2$ is combined with prehumidified (with water vapor) hydrogen in the amount corresponding to 2.1 kg/cm$^2$ hydrogen partial pressure. Said solution and hydrogen are charged to the top of a tower of corrosion resistant metal (e.g., titanium) packed with particulate (mixture of 4 to 8 mesh, U.S. Standard Sieve, particles of 0.5 wt. % Pd on carbon) hydrogenation catalyst held in place by a corrosion resistant metal (e.g., titanium) screen plate. The mixture of solution and hydrogen are permitted to flow downward through the catalyst bed at a space velocity of 1300 kg of solution per hour per cubic meter of catalyst bed.

The solution flowing from the bottom of the hydrogenation tower is degassed to remove hydrogen, filtered to remove catalyst particles which may have by attrition, split-off from the catalyst bed particles. The catalyst and hydrogen free solution is cooled in three steps of decompression to a final temperature of 130° C. and a gauge pressure of 2.4 kg/cm$^2$ by evaporation of solvent components, mainly water. Such vapors so generated are condensed and the condensates are not returned to the decompression step. By such cooling and attendant concentrating there is provided the precipitation of about 99% of the dissolved terephthalic acid. The resulting suspension of terephthalic acid precipitate is subjected to solid-liquid separation (e.g., by centrifugation filtration) to recover the terephthalic acid precipitate at said 130° C. temperature and 2.4 kg/cm$^2$ gauge pressure.

The recovered terephthalic acid is slurry washed with hot (100° C.) water. The washed product is recovered by filtration and dried.

The foregoing process is capable of producing dry terephthalic acid product having a 4-carboxybenzaldehyde content of less than 10 weight parts per million weight parts (ppm) of terephthalic acid, an optical density (340 nm light) value of less than 1.0, (e.g. from 0.01 to 0.5) and a color b-value of from −0.5 to +0.5. The present limit of detectability of 4-carboxybenzaldehyde in terephthalic acid is 10 ppm.

EXAMPLE 4

The process of Example 3 is repeated except that the 5.99 kg/hr. of fluid oxidation effluent is degassed at a final temperature of 220° C. and gauage pressure of 23 kg/cm$^2$ and then diluted with 10.74 kg/hr. of water at 220° C. and 23 kg/cm$^2$ to provide, for dissolving the 1.727 kg/hr. of solids, 15.36 kg/hr. solvent comprising 25 weight percent benzoic acid and 75 weight percent water. The diluted effluent contains 11.24 weight parts solids per 100 weight parts of solvent. Such diluted effluent is heated to 245° C. under a gauge pressure of 36 kg/cm$^2$ and maintained at those conditions until all the solids dissolve. To the resulting solution there is added prehumidified hydrogen to a hydrogen partial pressure of 0.8 kg/cm$^2$. The solution containing the hydrogen flows through a catalyst bed such as described in Example 3 but the particulate catalyst has 0.2 wt. % Pd on carbon and the solution flows at a rate of 600 kg/hr. per cubic meter of catalyst. The catalyst-free hydrogenated solution is processed as described in Example 3 to recover high purity terephthalic acid.

By the process of Example 4 a highly pure terephthalic acid product containing less than 10 ppm (weight basis) of 4-carboxybenzaldehyde, an optical density (340 nm light) value within the range of from 0.01 to 0.5 and a color b-value of from −0.5 to +0.5.

The invention claimed is:

1. The production of high purity iso- or terephthalic acid from the oxidation of m- or p-xylene with air in the presence of a combination of bromine with cobalt and manganese and a solvent comprising 85 to 97% benzoic acid and 15 to 3 percent water at a temperature in the range of from 175° C. up to 235° C. and a gauge pressure in the range of from 6 up to 25 kg/cm$^2$ to obtain a fluid effluent containing in addition to suspended iso- or terephthalic acid and dissolved catalyst components partial and co-oxidation products which are oxygen-containing aromatic compounds; characterized in that the fluid oxidation effluent is diluted with water to provide a solvent system comprising from 25 up to 75 weight percent water and from 75 down to 25 weight percent benzoic acid, the diluted effluent is heated to a temperature at which all the solids in the oxidation effluent are dissolved in said solvent system at a pressure to maintain said solvent system in the liquid phase, hydrogenating said solution in the presence of a Group VIII noble metal catalyst, separating the hydrogenated solution from the catalyst, precipitating iso- or terephthalic acid from the separated solution to form a suspension of said precipitate in the mother liquor portion of said solution, separating the precipitate from the catalyst-free mother liquor, washing the separated precipitate, and drying the washed iso- or terephthalic acid precipitate.

2. The process of claim 1 further characterized in that the hydrogenation catalyst comprises solid particles having metallic palladium disposed on the surface of a carbon support.

3. The process of claim 2 further characterized in that the oxidation effluent is diluted with an amount of water to provide a solvent comprising 50 percent each of benzoic acid and water.

4. The process of claim 2 further characterized in that iso- or terephthalic acid is precipitated from the hydrogen and catalyst free solution in three decompression steps by evaporating solvent components at successively lower pressure.

5. The process of claim 2 further characterized in that terephthalic acid is precipitated from the hydrogen and catalyst free solution in three decompression steps each operated at successively lower pressure to a final temperature of from 130° up to 150° C. by evaporation and removal of solvent components from each step.

6. The process of claim 2 further characterized in that the amount of hydrogen added to the solution resulting from heating of the diluted fluid oxidation effluent is equivalent to a hydrogen partial pressure of from 0.7 up to 7 kg/cm$^2$.

7. The process of claim 1 further characterized in that the weight ratio of 85-97 percent benzoic acid—15 to 3 percent water solvent to p-xylene is in the range of from 3.0 to 6.0 weight parts of said solvent per 1.0 weight part of p-xylene, the fluid oxidation effluent is diluted with water to provide a solvent comprising 50 weight percent each of water and benzoic acid, the diluted fluid effluent is heated to a temperature in the range of from 250° C. up to 280° C. to dissolve all the solids present in the fluid oxidation effluent, the hydrogen added to the solution is equivalent to a hydrogen partial pressure of from 0.7 up to 7 kg/cm$^2$, and the hydrogen and catalyst free solution is cooled in three steps of successively lower pressure to a final temperature of from 130° up to 150° C. by evaporating solvent components in each step and removing the resulting vapors from each step to precipitate terephthalic acid, and the separated terephthalic acid is washed with water and dried.

* * * * *

UNITED STATES PATENT OFFICE
CERTIFICATE OF CORRECTION

Patent No. 4,675,438　　　　　　　　　　Dated June 23, 1987

Inventor(s) Michael M. Schwartz & Leonard E. Stark

It is certified that error appears in the above-identified patent and that said Letters Patent are hereby corrected as shown below:

Column 6, Line 38, "3 18" should be --3.18--

Column 10, Line 3, "0.15.p" should be ---0.15--

Signed and Sealed this

Thirteenth Day of October, 1987

Attest:

DONALD J. QUIGG

*Attesting Officer*　　　　*Commissioner of Patents and Trademarks*